United States Patent [19]

Fukaya et al.

[11] Patent Number: 4,868,201

[45] Date of Patent: Sep. 19, 1989

[54] INDOLEACETIC ACID DERIVATIVES USED AS ANTI-INFLAMMATORIES

[75] Inventors: Chikara Fukaya, Osaka; Youichiro Naito, Kyoto; Shuichi Hanada, Suita; Masahiro Watanabe, Akashi; Kazumasa Yokoyama, Toyonaka, all of Japan

[73] Assignee: The Green Cross Company, Osaka, Japan

[21] Appl. No.: 42,924

[22] Filed: Apr. 27, 1987

Related U.S. Application Data

[63] Continuation-in-part of Ser. No. 788,445, Oct. 17, 1985, abandoned.

[30] Foreign Application Priority Data

Oct. 22, 1984 [JP] Japan ................. 59-222452

[51] Int. Cl.$^4$ .......................... A61K 31/405
[52] U.S. Cl. .................... 514/420; 548/500
[58] Field of Search .................. 548/500; 514/420

[56] References Cited

U.S. PATENT DOCUMENTS

| 3,468,907 | 9/1969 | Sherlock | 548/500 X |
| 4,104,278 | 8/1978 | Boltze et al. | 548/500 |
| 4,459,415 | 7/1984 | Boltze | 548/500 X |

FOREIGN PATENT DOCUMENTS

| 2740852 | 3/1979 | Fed. Rep. of Germany. | |
| 0036745 | 11/1970 | Japan | 548/500 |

Primary Examiner—David B. Springer
Attorney, Agent, or Firm—Cushman, Darby & Cushman

[57] ABSTRACT 1-(fluoro- or perfluoro lower alkyl-substituted benzoyl)-5-methoxy-2-methyl-1H-indole-3-acetic acid carboxymethyl ester is found to have antiinflammatory and analgestic activity with less side effects on gastrointestinal traces than its homologue, acematacin or indometacin.

11 Claims, No Drawings

INDOLEACETIC ACID DERIVATIVES USED AS ANTI-INFLAMMATORIES

This is a continuation in part application of Application Ser. No. 788,445 filed Oct. 17, 1985, now abandoned.

This invention relates to a novel indoleacetic acid derivative useful as an antiinflammatory and analgesic agent. More particularly, this invention relates to an indoleacetic acid derivative represented by the general formula

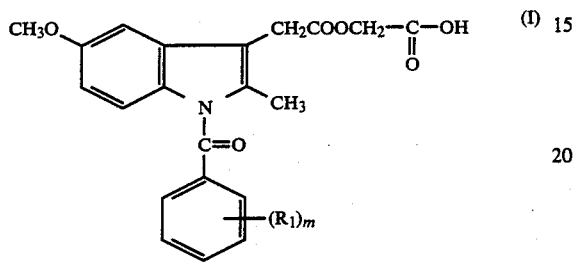

wherein $R_1$ is a fluorine atom or a perfluoro lower alkyl group and m is an integer of 1 or 2.

Heretofore, an indoleacetic acid derivative having an inflammatory and analgesic activity, such as 1-(4-chlorobenzoyl)-5-methoxy-2-methyl-1H-indole-3-acetic acid (so-called indometacin), has been made into a medical preparation for oral administration or as a suppository in its form of a free carboxylic acid and widely used clinically as such preparation. However, the use of such preparations often causes serious side effects in gastrointestinal tracts, so that various derivatives have been proposed for the purpose of reducing the side effects. U.S. Pat. No. 3,845,210 to Sato et al claims to comprise an analogous indoleacetic acid compound to the indometacin, in which 4-chlorobenzoyl moiety is replaced by 4-fluorobenzoyl. However, no such compound is disclosed. An example of such derivatives having a lower side effect is 1-(4-chlorobenzoyl)-5-methoxy-2-methyl-1H-indole-3-acetic acid carboxymethyl ester (called acemetacin) which is originally disclosed in U.S. Pat. Nos. 3,910,952, 4,104,278 and 4,459,415 to Bolze. However, the purpose has not been fully attained up to the present.

An object of this invention is to provide an indoleacetic acid derivative having reduced side effects on gastrointestinal tracts and excellent antiinflammatory and analgesic effects.

This invention relates to a novel indoleacetic acid derivative represented by the general formula (I).

In the general formula (I), $R_1$ is a fluorine atom or a lower perfluoroalkyl group and may be present in a number of 1 or 2, preferably 1 as the substituent for the hydrogen atom(s) of the phenyl group. The position of the phenyl group to which the substituent is attached may be any position, but p-position is preferable. The alkyl moiety in the lower perfluoroalkyl group is preferably those having 1 to 3 carbon atoms, namely a perfluorinated methyl, ethyl, n-propyl or isopropyl group, and particularly preferably a perfluoro methyl group.

The indoleacetic acid derivative of the formula (I) can be prepared, for example, by the following reaction schema:

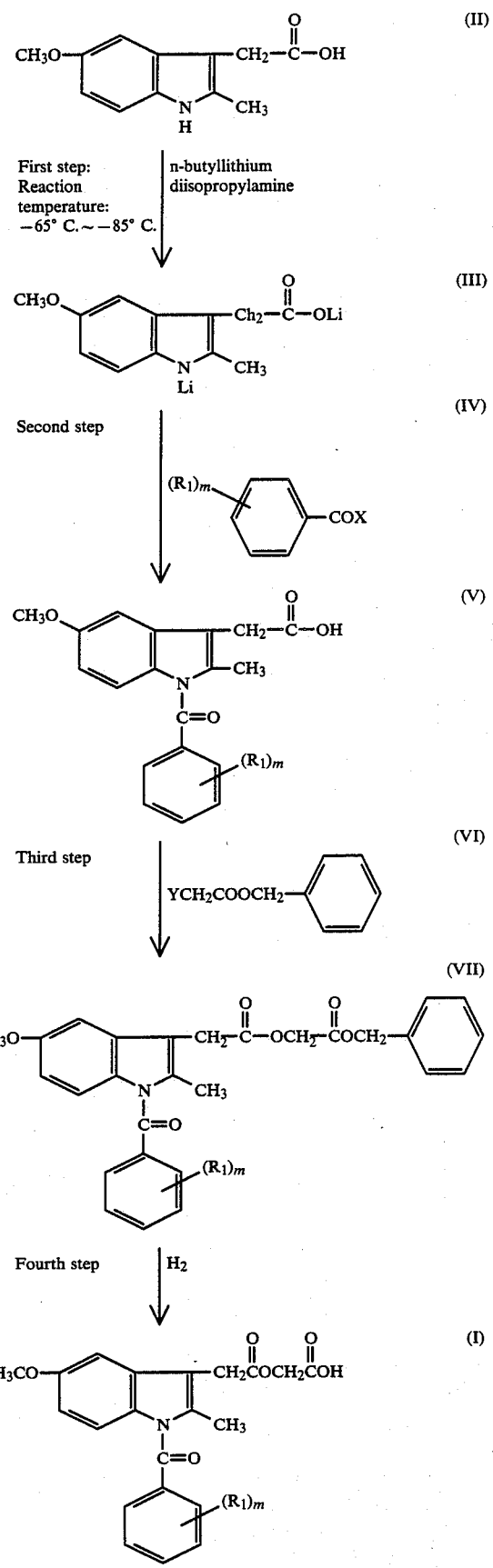

In the above formulas, X represents a halogen (preferably chlorine atom), Y represents a halogen (preferably iodine atom) and $R_1$ and m are the same as defined above.

The first step is the step of deriving the compound (III) from the compound (II), and is conducted in the presence of n-butyllithium and diisopropylamine. The reaction of this step is carried out under cooling at $-60°$ to $-85°$ C. for 20 to 50 minutes preferably in the presence of a solvent such as tetrahydrofuran.

The second step is the reaction of the compound (III) with the compound (IV) to give the compound (V). The reaction of this step is carried out at room temperature for 5 to 15 hours in a solvent, for example, one similar to that used in the first step.

The compound (V) thus produced can be purified and isolated from the reaction mixture according to a common procedure such as chromatography and recrystalization, and undergoes the third step of which reaction is already known.

The third step is the reaction of the compound (V) with the compound (VI) to give the compound (VII). This step is preferably conducted in the presence of tetrabutylammonium hydrogen sulfate. The reaction of this step is carried out at room temperature for 1 to 3 hours preferably in a solvent such as methylene chloride.

The fourth step is the step of deriving the compound (I) from the compound (VII) by applying the conventional catalytic hydrogenation method. The reaction is carried out for 20 to 60 minutes in the presence of a catalyst such as palladium/carbon in an inert solvent such as ethyl acetate about at a room temperature under hydrogen atmosphere. The indoleacetic acid derivative (I) thus formed can be isolated and purified by conventional means such as solvent extraction, recrystallization and chromatography.

The indoleacetic acid derivative (I) or its pharmacologically acceptable salt exhibits excellent antiinflammatory and analgesic effects and shows only a very little gastroenteric trouble for mammals such as humans, horses, dogs, mice and rats. For example, in a suppression experiment against carrageenin edema using rats, the $ED_{40}$ of the Compound 1 referred to later in Example 1, an indoleacetic acid derivative (I), is 1.7 mg/kg p.o. as compared with 2.8 mg/kg p.o. of indometacin, thus showing a higher suppression effect than that of indometacin. On the other hand, the gastric trouble caused by the Compound 1 is about one fourth of that by indometacin and the small-intestinal trouble is about one half of that caused by indometacin. As compared with acemetacin, the antiinflammatory effect of the Compound 1 is about three times and the gastroenteric trouble is one-half, respectively.

Thus, the indoleacetic acid derivative (I) shows an extremely excellent antiinflammatory and analgesic effect with very low side effects and is useful as an inflammatory and analgesic agent.

The indoleacetic acid derivative (I) of this invention is used for antiinflammation and analgesia in admixture with conventional adjuvants. The administration thereof can be conducted by conventional methods known in the art including oral administration (in the form of tablets, capsules, granules and sirups); subcutaneous, intramuscular or intravenous injections; applications as known agents for external use; and rectal administration using suppositories. The does should be an amount sufficient for the antiinflammatory and analgesic effect to be exhibited and, though it may very depending, for examples, on the animals to be treated, symptoms, administration routes and dosage forms, is 0.05 to 1 mg/kg, and preferably 0.1 to 0.3 mg/kg of body weight in one oral administration in general. The number of times of administration may be suitably selected according to the dose per day, the dosage schedule, the symptom, etc.

The indoleacetic acid derivative (I) of this invention can also be used in combination with other antiinflammatory and analgesic agents.

The present invention is explained in detail by way of the following Examples not limiting the invention.

(1) Synthesis of 1-(4-fluorobenzoyl)-5-methoxy-2-methyl-1H-indole-3-acetic acid:

Dry isopropylamine, 4.5 ml (32 mmol), was dissolved in dry tetrahydrofuran, 50 ml, and the resulting solution was cooled to -78° C. Under nitrogen atmosphere, 20.6 ml of 1.55N n-butyllithium solution (32 mmol) in hexane was added dropwise to the above solution with stirring, and the mixture was further stirred at $-78°$ C. for 30 minutes. Then, a solution of 3.5 g (16 mmol) of 5-methoxy-2-methyl-indole-3-acetic acid dissolved in 50 ml of dry tetrahydrofuran was added dropwise to the above mixture at $-78°$ C. with stirring. After completion of the dropwise addition, the resulting mixture was further stirred at $-78°$ C. for 30 minutes. Then, 3.33 g (20.8 mmol) of 4-fluorobenzoyl chloride dissolved in 50 ml of dry tetrahydrofuran was added dropwise to the solution with stirring at $-78°$ C. After completion of the addition, the resulting reaction solution was gradually brought back to room temperature and further stirred overnight at the temperature. The reaction mixture obtained was poured into 0.1N hydrochloric acid and extracted with ethyl acetate. The extract was washed with water, then with saturated aqueous sodium chloride solution, and dried over anhydrous magnesium sulfate. After distilling off the solvent, the residue was purified by silica gel column chromatography (using a solvent mixture of chloroform/methanol=26/1 as the eluent) and recrystallized from diethylether to give 2.9 g (yield: 52%) of the compound mentioned in (1) above, melting at 143° to 144° C.

(2) Synthesis of 1-(4-fluorobenzoyl)-5-methoxy-2-methyl-1H-indole-3-acetic acid benzyloxycarbonylmethyl ester:

To 8.5 ml of 1N aqueous sodium hydroxide solution, was added at 0° C. 1.45 g (4.2 mmol) of tetrabutylammonium hydrogen sulfate and the mixture was stirred. Then, 1.46 g (4.1 mmol) of the compound (I) obtained in the preceding step was added thereto at room temperature and the mixture was stirred. The resulting reaction solution was extracted with 30 ml of methylene chloride, the extract was dried over anhydrous magnesium sulfate and filtered, and the filtrate was cooled to 0° C. Then, a solution of 1.42 g (4.1 mmol) of benzyl iodoacetate in 4 ml of methylene chloride was added dropwise thereto with stirring. After completion of the dropwise addition, the resulting mixture was stirred at 0° C. for 30 minutes and further at room temperature for 2.5 hours. After distilling off the solvent, the residue was purified by silica gel column chromatography (using a solvent mixture of ethyl acetate/hexane=¼ as the eluent) to obtain 1.57 g (yield: 76%) of the compound (2) mentioned above.

(3) Synthesis of 1-(4-fluorobenzoyl)-5-methoxy-2-methyl-1H-indole-3-acetic acid carboxymethyl ester:

Into 80 ml of ethyl acetate, was dissolved 1.57 g (3.1 mmol) of the compound (2) obtained in the preceding step, and 0.75 g of 10% palladium on carbon powder was added thereto. The resulting solution was subjected to hydrogenation with stirring for 30 minutes under hydrogen atmosphere at room temperature. The palladium-carbon powder was removed by filtration. Recrystallization from ethyl acetate-hexane gave 0.89 g (yield: 69%) of the compound mentioned in (3) above (hereinafter referred to as "Compound 1"), melting at 144.5° to 145° C. The data on $^1$HNMR and IR spectra of the Compound 1 are shown below.

$^1$HNMR (CDCl$_3$+DMSO-d$_6$): δ 7.91-6.50 (m, 7H), 4.56 (s, 2H), 3.86-3.70 (5H), 2.30 (s, 3H) IR (KBr, cm$^{-1}$): 3200-2600, 1730, 1670, 1600, 1210, 850, 800

EXAMPLE 2

The Compounds 2 to 9 mentioned below were prepared in the same manner using the raw materials in same molar amounts as in Example 1, provided that in place of 4-fluorobenzoyl chloride various fluoro or trifluoromethyl benzoyl chlorides were respectively used to obtain them.

1-(2-Fluorobenzoyl)-5-methoxy-2-methyl-1H-indole-3-acetic acid carboxymethyl ester (Compound 2)

m.p.: 172.5°-173° C. $^1$HNMR (CDCl$_3$ +DMSO-d$_6$): δ 9.11 (brs, 1H), 7.70-6.52 (m, 7H), 4.56 (s, 2H), 3.80 (s, 3H), 3.74 (s, 2H), 2.28 (s, 3H) IR (KBr, cm$^{-1}$): 3300-2700, 1740, 1710, 1670, 1615, 1155, 760

1-(3-Fluorobenzoyl)-5-methoxy-2-methyl-1H-indole-3-acetic acid carboxymethyl ester (Compound 3)

m.p.: 134°-136° C. $^1$HNMR (CDCl$_3$): δ 8.53 (s, 1H), 7.59-6.53 (m, 7H), 4.67 (s, 2H), 3.90-3.73 (5H), 2.35 (s, 3H) IR (KBr, cm$^{-1}$): 3550-3300, 3100-2850, 1755, 1720, 1670, 1615, 1590, 1170, 795, 750

1-(2-Trifluoromethylbenzoyl)-5-methoxy-2-methyl-1H-indole-3-acetic acid carboxymethyl ester (Compound 4)

m.p.: 121°-122° C. $^1$HNMR (CDCl$_3$): δ 9.58 (s, 1H), 7.95-6.55 (m, 7H), 4.65 (s, 2H), 3.79 (s, 3H), 3.73 (s, 2H), 2.20 (s, 3H) IR (KBr, cm$^{-1}$): 3600-3300, 3000-2875, 1740, 1690, 1615, 1320, 1165, 770

1-(3-Trifluoromethylbenzoyl)-5-methoxy-2-methyl-1H-indole-3-acetic acid carboxymethyl ester (Compound 5)

m.p.: 136°-138° C. $^1$HNMR (CDCl$_3$ +DMSO-d$_6$): δ 8.06-6.52 (m, 7H), 4.60 (s, 2H), 3.93-3.68 (5H), 2.33 (s, 3H) IR (KBr, cm$^{-1}$): 3600-3300, 3000-2875, 1755, 1740, 1690, 1615, 1310, 1165, 780

1-(4-Trifluoromethylbenzoyl)-5-methoxy-2-methyl-1H-indole-3-acetic acid carboxymethyl ester (Compound 6)

m.p.: 166.5°-167° C. $^1$HNMR (CDCl$_3$ +DMSO-d$_6$): δ 7.81 (s, 4H), 7.12-6.51 (m, 3H), 4.56 (s, 2H), 3.92-3.66 (5H), 2.22 (s, 3H) IR (KBr, cm$^{-1}$): 3250-2800, 1750, 1735, 1680, 1615, 1605, 1325, 1170, 855, 850, 800

1-(2,4-Difluorobenzoyl)-5-methoxy-2-methyl-1H-indole-3-acetic acid carboxymethyl ester (Compound 7)

m.p.: 156°-157° C. $^1$HNMR (CDCl$_3$ +DMSO-d$_6$): δ 7.76-5.87 (m), 4.56 (s, 2H), 4.04-3.56 (5H), 2.27 (s, 3H) IR (KBr, cm$^{-1}$): 3300-2800, 1740, 1665, 1610, 1230, 1150, 870, 800

1-(2,6-Difluorobenzoyl)-5-methoxy-2-methyl-1H-indole-3-acetic acid carboxymethyl ester (Compound 8)

m.p.: 185.5°-186.5° C. $^1$HNMR (CDCl$_3$ +DMSO-d$_6$): δ 9.40 (brs, 1H), 7.76-6.58 (m, 6H), 4.55 (s, 2H), 3,80 (s, 3H), 3.72 (s, 2H), 2.24 (s, 3H) IR (KBr, cm$^{-1}$): 3250-2800, 1750, 1720, 1680, 1630, 1170, 795

1-(3,4-Difluorobenzoyl)-5-methoxy-2-methyl-1H-indole-3-acetic acid carboxymethyl ester (Compound 9)

m.p.: 128°-129° C. IR (KBr, cm$^{-1}$): 3100-2800, 1740, 1680, 1615, 1235, 1160

Among the indoleacetic acid derivatives of the present invention, Compounds 1 and 6 are most preferable.

EXPERIMENTAL EXAMPLE 1 (Antiinflammatory effect)

In one experimental test male rats of SD strain (in groups of 5) were used. The animals were subcutaneously administered 0.1 ml of 1% carrageenin solution in physiological saline at the sole of their right hind legs to cause the onset of edema in their feet. The medicine to be tested was orally administered to each individual in the group 30 minutes before and 1 hour after the administration of carrageenin, respectively and the volume of the foot was measured at the time 3 hours after the carrageenin administration. The degree of suppression of inflammation (edema suppresion) was determined in terms of the suppression rate relative to the foot volume of the rat group which had been given 0.5% CMC solution.

The experiments including contrast with administration of carrageenin only were repeated 2 or 3 times with same or different amounts of the medicine for one group. The degree of suppression of inflammation (edema) is calculated by the following equation:

$$\text{Suppression rate (\%)} = \frac{E_C - E_S}{E_C} \times 100$$

wherein $E_C$ is an average edema volume increase rate after carrageenin administration of the control group, and $E_S$ is that after medicine administration.

Based on the edema volume suppression rate (%) - dose (mg/kg), dose-responsive relationship is plotted in the semi-logarithum co-ordinate system in which doses are taken in logarithum on the abscissa, and edema suppression rate (%) is taken on the normal ordinate. The method of least squares applies to the plots to obtain a regression line. The dose responsive to edema suppression rate 40% (ED$_{40}$) is taken from the regression line in each of the repeated tests. The average value of all of the ED$_{40}$'s with respect to the respective medicines is taken as the ED$_{40}$ thereof.

The edema suppression rate (%) obtained is shown in Table 1, and the ED$_{40}$ calculated is in Table 2, with respect to the respective medicines.

TABLE 1

| | Tests | Dose (mg/kg of animal weight) Each before and after carrageenin administration | Edema Suppression rate (%) |
|---|---|---|---|
| Indomethacine | 1st | 0.3 | 15 |
| | | 3 | 52 |
| (Bolze: | 2nd | 0.3 | 26 |
| U.S. Pat. | | 1 | 46 |
| NO. 4,459,415) | | 3 | 58 |
| | 3rd | 0.3 | 14 |
| | | 3 | 49 |
| Acemethacine | 1st | 1 | 31 |
| (Bolze: ibid) | | 3 | 41 |
| | | 10 | 56 |
| | 2nd | 1 | 26 |
| | | 3 | 48 |
| | | 10 | 68 |
| Sato et al compound | 1st | 0.3 | 9 |
| | | 1 | 33 |

TABLE 1-continued

| Tests | Dose (mg/kg of animal weight) Each before and after carrageenin administration | Edema Suppression rate (%) |
|---|---|---|---|
| 1-(4-fluoro-benzoyl)-2-5-methoxy 3-indolylacetic acid (not disclosed but falls into Sato et al claim) | 2nd | 3 | 32 |
| | | 0.3 | 10 |
| | | 1 | 27 |
| | | 3 | 49 |
| Compound 1 (Present invention) | 1st | 0.1 | 15 |
| | | 0.3 | 32 |
| | | 1 | 55 |
| | | 3 | 65 |
| | 2nd | 0.3 | 25 |
| | | 1 | 43 |
| | | 3 | 46 |
| | 3rd | 0.3 | 16 |
| | | 1 | 37 |
| | | 3 | 67 |
| Compound 6 (Present invention) | 1st | 1 | 0 |
| | | 3 | 32 |
| | | 10 | 63 |
| | 2nd | 1 | 27 |
| | | 3 | 40 |

TABLE 2

| | ED$_{40}$ (mg/kg) | | | |
|---|---|---|---|---|
| | Tests | | | |
| | 1st | 2nd | 3rd | Average |
| Indomethacine | 3.0 | 1.4 | 4.0 | 2.8 |
| Acemethacine | 4.8 | 4.6 | — | 4.7 |
| Sato et al compound | 6.0 | 3.4 | — | 4.7 |
| Compound 1 | 1.0 | 2.0 | 2.0 | 1.7 |
| Compound 6 | 8.0 | 6.0 | — | 7.0 |

EXPERIMENTAL EXAMPLE 2 (Side effect: Gastric trouble)

Male rats of SD strain (in groups of 7) were deprived of food for 24 hours, then orally administered the medicine to be tested in amounts shown in Table 3, and further kept deprived of food and water for 5 hours. Then, the animals were killed by carbon dioxide gas and the stomachs were exicsed from the animals with the lower part of the esophagus and the upper part of the duodenum attached thereto. They were fixed with 1% formaline, incised along the greater curvature of the stomach and examined for the state of hemorrhage and the state of ulcer.

In the examination, the ratings shown below were used as the ulcer index.
0: No change
1: Hemorrhagic or inflamed state
2: 1 to 3 ulcers
3: 4 to 10 ulcers
4: 11 or more ulcers The ulcer formation ratings responsive to doses were calculated and shown in Table 3.

TABLE 3

| | Dose (mg/kg) | Average ulcer formation ratng (n = 7) |
|---|---|---|
| Indomethacine | 3 | 2.1 ± 1.0 |
| | 6 | 3.4 ± 0.5 |
| | 10 | 4.0 ± 0 |

TABLE 3-continued

| | Dose (mg/kg) | Average ulcer formation ratng (n = 7) |
|---|---|---|
| Acemethacine | 3 | 0.9 ± 0.9 |
| | 10 | 3.0 ± 0.8 |
| | 30 | 3.9 ± 0.4 |
| Sato et al compound | 3 | 0.8 ± 0.6 |
| | 10 | 2.6 ± 0.5 |
| | 30 | 3.8 ± 0.4 |
| Compound 1 | 3 | 0.6 ± 1.0 |
| | 10 | 2.0 ± 1.0 |
| | 30 | 3.7 ± 0.5 |
| Compound 6 | 3 | 1.1 ± 0.9 |
| | 10 | 1.3 ± 0.8 |
| | 30 | 1.6 ± 0.8 |

Based on the ulcer formation in each dose, the least squares method was applied, and a curve was produced by taking dose on logarithm abscisa and ulcer index on normal ordinate with respect to each dose of the medicines. The curve was modified to obtain a regression line from which dose responsive to ulcer formation rating 2 ($UD_{50}$) was obtained.

The result is shown in Table 4, in which the ratio of the $UD_{50}$ to $ED_{40}$ (in Table 2) is given for demonstrating the therapeutic effect of each medicine. It will be noted that relatively, the larger the ratio, the smaller the side effect is.

TABLE 4

| | $UD_{50}$ (mg/kg) | $UD_{50}/ED_{40}$ |
|---|---|---|
| Indomethacine | 2.7 | 0.94 |
| Acemethacine | 5.9 | 1.23 |
| Sato et al compound | 7.0 | 1.49 |
| Compound 1 | 9.4 | 5.54 |
| Compound 6 | 150 | 21.42 |

EXPERIMENTAL EXAMPLE 3 (Side effect: Small-intestinal trouble)

Male rats of SD strain (in groups of 10) were orally administered the medicine to be tested and, after 3 days of normal breeding, killed by carbon dioxide gas. The small-intestinal parts (duodenum, jejunum and ileum) were excised from the animals, fixed with 1% formaline and then incised to examine the state of ulcer and that of the adhesion of intestinal tracts with the naked eye. When at least one ulcer was observed, the ulcer-forming effect was judged as positive. The positive rates responsive to doses were calculated and shown in Table 5. The $UD_{50}$ values (the dose responsive to positive rate 50%) were calculated according to the method of Litchfield & Wilcoxon and shown in Table 6 together with the ratio of $UD_{50}$ to $ED_{40}$.

TABLE 5

| Drug. | Dose (mg/kg) | Positive rate (n = 10) |
|---|---|---|
| Indometacin | 3 | 0/10 |
| | 6 | 1/10 |
| | 8 | 8/10 |
| | 10 | 10/10 |
| Acemetacin | 3 | 0/10 |
| | 6 | 3/10 |
| | 10 | 9/10 |
| | 30 | 10/10 |
| Compound 1 | 3 | 0/10 |
| | 10 | 0/10 |
| | 15 | 9/10 |
| | 18 | 9/10 |

TABLE 5-continued

| Drug. | Dose (mg/kg) | Positive rate (n = 10) |
| --- | --- | --- |
| | 30 | 10/10 |
| Compound 6 | 3 | 0/10 |
| | 10 | 1/10 |
| | 30 | 8/10 |

TABLE 6

| | $UD_{50}$ (mg/kg) | $UD_{50}/ED_{40}$ |
| --- | --- | --- |
| Indometacin | 7 | 2.5 |
| Acemetacin | 7 | 1.49 |
| Compound 1 | 14 | 8.25 |
| Compound 6 | 19 | 2.71 |

The indoleacetic acid derivative (I) may be formulated into an oral administration preparation admixed with a conventional physiologically acceptable diluent, and can be orally administered to a mammal for treating inflammation without the side effects in gastrointestinal tracks.

PREPARATION EXAMPLE 1

1-(4-fluorobenzoyl)-5-methoxy-2-methyl-1H-indole-3-acetic acid carboxymethyl ester . . . 20 mg
  Magnesium stearate . . . 50 mg
  Lactose . . . 50 mg The ingredients listed above were composed to form a tablet each weighing 120 mg.

What is claimed is:

1. A process for treating inflammation in a mammal which comprises administrating to said mammal an effective amount of an idoleacetic acid derivative represented by the formula

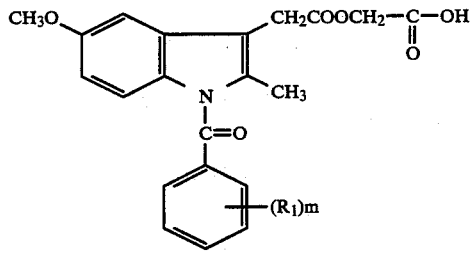

wherein $R_1$ is a fluorine atom or a $C_1$–$C_3$ perfluoroalkyl group and m is an integer of 1 or 2; and its pharmacologically acceptable salts.

2. The process of claim 1, wherein said mammal is administered an effective amount of the indoleacetic acid derivative represented by the formula

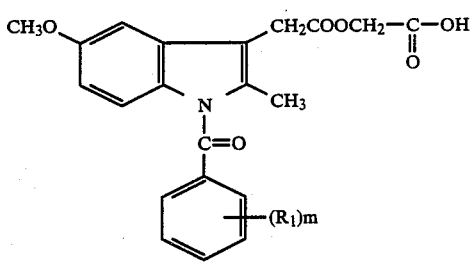

wherein $R_1$ is a fluorine atom or a trifluoromethyl group.

3. The process of claim 1, wherein said mammal is administered an effective amount of 1-(4-fluorobenzoyl)-5-methoxy-2-methyl-1H-indole-3-acetic acid carboxymethyl ester.

4. The process of claim 1, wherein said mammal is administered an effective amount of 1-(2-fluorobenzoyl)-5-methoxy-2-methyl-1H-indole-3-acetic acid carboxymethyl ester.

5. The process of claim 1, wherein said mammal is administered an effective amount of 1-(3-fluorobenzoyl)-5-methoxy-2-methyl-1H-indole-3-acetic acid carboxymethyl ester.

6. The process of claim 1, wherein said mammal is administered an effective amount of 1-(2,4-difluorobenzoyl)-5-methoxy-2-methyl-1H-indole-3-acetic acid carboxymethyl ester.

7. The process of claim 1, wherein said mammal is administered an effective amount of 1-(2,6-difluorobenzoyl)-5-methoxy-2-methyl-1H-indole-3-acetic acid carboxymethyl ester.

8. The process of claim 1, wherein said mammal is administered an effective amount of 1-(2-trifluoromethylbenzoyl)-5-methoxy-2-methyl-1H-indole-3-acetic acid carboxymethyl ester.

9. The process of claim 1, wherein said mammal is administered an effective amount of 1-(3-trifluoromethyl-benzoyl)-5-methoxy-2-methyl-1H-indole-3-acetic acid carboxymethyl ester.

10. The process of claim 1, wherein said mammal is administered an effective amount of 1-(4-trifluoromethylbenzoyl)-5-methoxy-2-methyl-1H-indole-3-acetic acid carboxymethyl ester.

11. The process of claim 1, wherein said mammal is administered an effective amount of 1-(3,4-difluorobenzoyl)-5-methoxy-2-methyl-1H-indole-3-acetic acid carboxymethyl ester.

* * * * *